(12) United States Patent  
Chin

(10) Patent No.: US 6,277,137 B1
(45) Date of Patent: Aug. 21, 2001

(54) TISSUE SEPARATION CANNULA WITH DISSECTION PROBE AND METHOD

(75) Inventor: Albert K. Chin, Palo Alto, CA (US)

(73) Assignee: Origin Medsystems, Menlo Park, CA (US)

( * ) Notice: Subject to any disclaimer, the term of this patent is extended or adjusted under 35 U.S.C. 154(b) by 0 days.

(21) Appl. No.: 09/436,936

(22) Filed: Nov. 8, 1999

Related U.S. Application Data

(63) Continuation of application No. 08/907,691, filed on Aug. 8, 1997, now Pat. No. 5,980,549, which is a continuation of application No. 08/593,533, filed on Jan. 24, 1996, now abandoned, which is a continuation-in-part of application No. 08/502,494, filed on Jul. 13, 1995, now abandoned, which is a continuation-in-part of application No. 08/421,481, filed on Apr. 12, 1995, now Pat. No. 5,591,183.

(51) Int. Cl.[7] .................................................. A61B 17/00
(52) U.S. Cl. .............................................................. 606/190
(58) Field of Search ..................................... 606/190, 191, 606/167, 194, 207

(56) References Cited

U.S. PATENT DOCUMENTS 5,980,549 * 11/1999 Chin ...................................... 606/190

* cited by examiner

Primary Examiner—Michael Buiz
Assistant Examiner—(Jackie) Tan-Uyen T. Ho
(74) Attorney, Agent, or Firm—Fenwick & West LLP

(57) ABSTRACT

A cannula includes a tubular body having a proximal end and distal blunt end, at least one lumen extending the length of the body, an endoscope having a lighted, viewing end disposed in the lumen near the distal end of the body, and a transparent, tissue-separating tip substantially covering the distal end of the body. The tissue-separating tip is slightly blunted to inhibit avulsion of tissue and lateral vessels along the dissected cavity formed thereby. Endoscopic viewing through the tip is enhanced by tapering the inner walls thereof to a cusp adjacent the blunt tip in order to reduce visual distortion. Alternatively, a cannula includes a dissection probe and a removable or deflectable tip for exposing the probe and endoscope to facilitate viewing and the dissection of connective tissue and lateral vessels along the dissected cavity. Methods of using such cannulas produce an elongated cavity along the course of a blood vessel for subsequent harvesting or other treatment of the isolated blood vessel. The dissection probe includes a partial ring that is substantially coaxially aligned with the generally cylindrical body of the cannula for passing along the vessel and past lateral branching vessels, and that is manipulatable at the distal end of the cannula in view of the endoscope which visualizes through the transparent tip. Where the vessel is an artery, an initial incision is made, for example, above the superior epigastric artery and the overlying tissue is bluntly dissected down to the superior epigastric artery to establish an initial portion of an elongated working cavity of bluntly-dissected tissue. Lateral arterial branches are doubly clipped or otherwise doubly occluded, and then severed to isolate the artery for use in revascularizing the coronary artery, for example, by transection of the superior epigastric or internal mammary artery and attachment of the transected end to the coronary artery downstream of a significant stenotic occlusion.

19 Claims, 14 Drawing Sheets

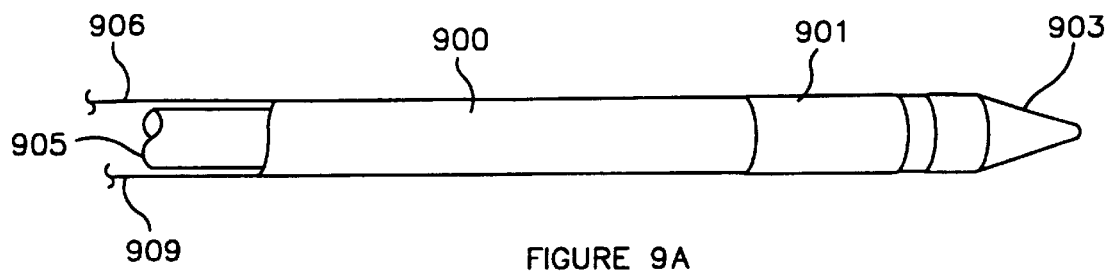
FIGURE 9A
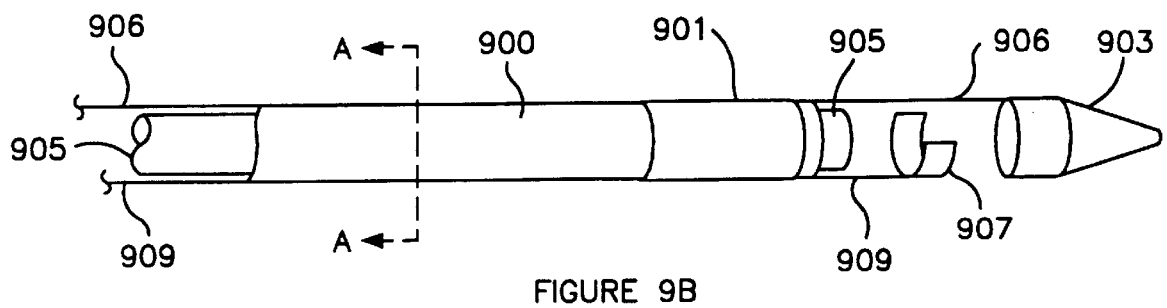
FIGURE 9B
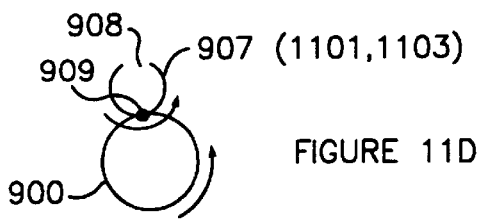
FIGURE 11D
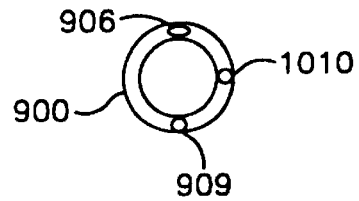
SECTION A—A
FIGURE 10
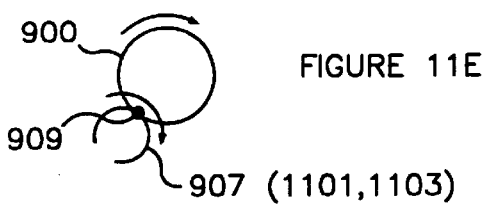
FIGURE 11E
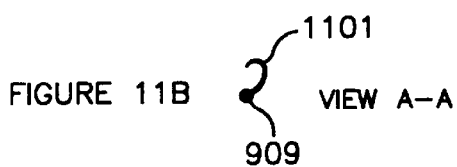
FIGURE 11B  VIEW A—A
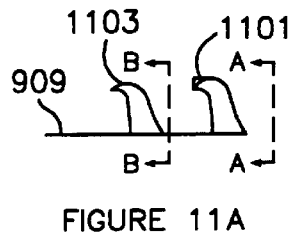
FIGURE 11A
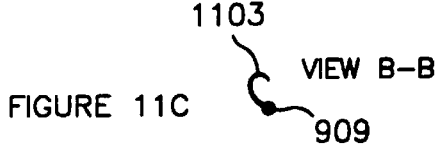
FIGURE 11C  VIEW B—B

TISSUE SEPARATION CANNULA WITH DISSECTION PROBE AND METHOD

RELATED APPLICATION

This is a continuation application of application Ser. No. 08/907,691 entitled "Tissue Separation Cannula with Dissection Probe and Method" filed on Aug. 8, 1997 U.S. Pat. No. 5,980,549, by Albert K. Chin, which is a continuation of application Ser. No. 08/593,533 filed on Jan. 24, 1996, now abandoned which is a continuation-in-part application of application Ser. No. 08/502,494 entitled "TISSUE SEPARATION CANNULA AND METHOD" filed on Jul. 13, 1995 now abandoned, by Albert K. Chin, and the subject matter hereof is continuation-in-part to the subject matter of application Ser. No. 08/421,481 entitled "CANNULA ASSEMBLY AND METHOD FOR PROGRESSIVELY DISSECTING TISSUE" filed on Apr. 12, 1995 U.S. Pat. No. 5,581,183 by Albert K. Chin, which prior applications are assigned to the same assignee as the present application and are incorporated herein by reference.

BACKGROUND OF THE INVENTION

1. Field of the Invention

The present invention relates generally to a tissue separation cannula used for forming an elongated cavity in tissue planes particularly along the course of a small blood vessel, and more specifically relates to a cannula having an endoscope for continuously visualizing the blunt dissection site through a tissue separating member which is transparent and has a tapered shape and is selectively removable from the cannula to facilitate dissection of tissue adjacent a blood vessel.

2. Description of Background Art

Present methods for the formation of an elongated cavity involve the use of blunt probes that are pushed through body tissue to accomplish the tissue dissection. The force exerted by the passage of mechanical probes may lead to blood vessel avulsion and trauma to tissue and internal organs.

The problem becomes acute when dissecting and harvesting blood vessels having a small diameter of about 3 to 8 mm. The techniques which are used for dissection of larger blood vessels such as the aorta are not applicable since the aorta is located in the retroperitoneum, bounded by the peritoneum on one side and the psoas muscle on the other side. An everting balloon placed in the infrarenal space located just below the kidney will track easily down the length of the aorta along a natural cleavage plane when inflated.

An everting type of balloon encounters difficulties when dissecting tissue adjacent a smaller-diameter vessel. This is due to the presence of less distinct planes that exist between small diameter blood vessels and the tissue that surrounds these vessels, as compared with the aorta and the tissue that surrounds the aorta. For example, if an everting balloon is placed adjacent to the saphenous vein in the leg, it usually skews dissection upon inflation rather than track along the vein. This is due to the amorphous nature of the fat and connective tissue that surrounds the saphenous vein.

Everting balloon catheters are known which are used for arterial dilation. (See, for example, U.S. Pat. No. 4,479,497 (Fogarty et al., Oct. 30, 1984) and U.S. Pat. No. 4,863,440 (Chin, Sep. 5, 1989)).

Double lumen everting balloon catheters, such as those disclosed in the Fogarty et al. '497 and the Chin '440 patents, have a through-lumen that slidably receives an endoscope. However, an endoscope used in conjunction with those disclosed catheters is unable to monitor the dissection process, since the endoscope lies within the central lumen proximal to the everting balloon. As the balloon everts from the catheter, the internal inflation pressure squeezes the walls of the balloon and closes off the distal viewing channel. Also, the area that requires monitoring during balloon dissection is located at the advancing front of the everting balloon. This area corresponds to the balloon/tissue interface that is subject to forces which cause tissue separation. Thus, an endoscope in the central lumen of existing double-lumen, everting balloon catheters is unable to view the area of tissue separation, since a double layer of balloon membrane lies between the endoscope and the tissue and blocks the endoscopic line of sight. This double layer obscures and distorts the viewing area of tissue separation.

Endoscopes have been disclosed for use in optical trocars such as in U.S. Pat. No. 5,385,572 (Nobles et al., Jan. 31, 1995) and EP 0 642 764 A1 (Sauer et al., published Mar. 15, 1995) and in harvesting blood vessels such as in U.S. Pat. No. 5,373,840 (Knighton, Dec. 20, 1994). The Nobles et al. '572 patent and the Sauer et al. '764 application disclose the use of sharp-tipped, metal cutting elements which extend outwardly from an endoscope positioned in the trocar. Control of the dissection is difficult because visualization of the vessel is obscured by the collapse of the tissue planes into the area between the cutting element and the endoscope. Furthermore, the risk of side vessel avulsion or trauma to the vessel is greatly increased by the orientation of the outwardly extending cutting elements.

The endoscope disclosed in Knighton '840 has a lateral dimension of a size sufficient to accommodate the blood vessel being harvested and at least one tool for use in harvesting the blood harvested. However, the failure of the endoscope to enlarge a cavity adjacent the blood vessel obscures viewing of the dissection area and manipulation of the vessel therein. The position of the viewing image relative to the tissue dissection area could obscure the identification of side vessels leading to an increased risk of vessel avulsion. Since the vessel is retrieved through the center of the endoscope, all side vessels must be severed for the endoscope to advance and the length of the vessel thus retrieved is limited substantially by the length of the body of the endoscope.

An instrument for penetrating body tissue, as disclosed in U.S. Pat. No. 5,271,380 (Riek, et al.), is equipped with a tapered tip of transparent material for viewing tissue penetrated by the tip using an optical unit which is positioned behind the tip. An instrument of this type may include a separate illumination channel that ends at the tip for illuminating tissue being penetrated.

SUMMARY OF THE INVENTION

The present invention provides a cannula for bluntly dissecting an elongated cavity in tissue particularly along the course of a vessel in a human or animal body. The cannula includes a tubular body having proximal closed end and distal blunt end and at least one lumen extending the length of the body. The cannula also includes an endoscope having a lighted, viewing end disposed in the lumen near the distal end of the body, and includes a transparent, tissue separating member, or blunt tip, substantially covering and selectively removable from the distal end of the body. The tissue separating member or blunt tip disposed on the distal end of the body includes internal walls that taper to a cusp to reduce visual distortion through the endoscope that is optically aligned with the tip.

A method is also disclosed for bluntly dissecting an elongated cavity particularly along the course of a vessel using a cannula. The method includes the steps of: bluntly dissecting an initial cavity; separating the tissue by advancing the cannula along the cavity with continuous, visual observation; repeating the prior step of separating the tissue at least until the cavity is sufficiently elongated to advance a balloon therein; and successively inflating and deflating a balloon within the cavity to enlarge the cavity along the course of the vessel. Following dissection of the cavity along the vessel, a counterincision is made at the far end of the cavity, for example, to place a second blunt tip balloon trocar and to allow introduction of dissection instruments. The tip of the cannula is advanced out of the body through the counterincision, and the tapered tip is detached leaving the cannula body in the dissected cavity. The endoscope resides inside the cannula body, and the endoscope and cannula body are selectively positioned as a single unit inside the dissected cavity to facilitate isolating and harvesting the vessel. The method further may include removing the cannula, then maintaining the elongated cavity using insufflated gas through a balloon cannula that seals the incisions against gas leakage, or using a structural balloon, or a mechanical structural support within the dissected cavity.

In another embodiment of the present invention, the method includes the steps of bluntly dissecting an initial cavity; sealing and inflating the cavity; and separating the tissue along the cavity assisted by continuous, visual observation while under inflation until the cavity is sufficiently elongated.

The isolated vessel, such as the saphenous vein, may be harvested and removed for use as a coronary artery or peripheral vascular bypass graft, or may be left in place as an in-situ femoropopliteal or femoral-distal graft. The side branches of the vein are ligated, clipped, or occluded in both applications. In the case of an in-situ graft, the valves in the vein are disrupted by means of a valvulotome.

BRIEF DESCRIPTION OF THE DRAWINGS

FIGS. 9A AND 9B are pictorial side views showing, respectively, assembled and dissembled configurations of another alternative embodiment of the present invention;

FIG. 10 is a cross sectional view of cannula of FIGS. 9A and 9B;

FIGS. 11A, 11B and 11C are, respectively, side and sectional views of an alternate dissection probe that may be used with the cannula shown in FIGS. 9A and 9B;

FIGS. 11D and 11E are end views of the dissection probe in orbital positions about the cannula body;

DESCRIPTION OF THE PREFERRED EMBODIMENT

In accordance with one embodiment of the present invention, a cannula includes a tubular body having proximal closed end and distal blunt end, at least one lumen extending the length of the body, an endoscope having a lighted, viewing end disposed in the lumen near the distal end of the body, and a transparent, tissue separating member substantially covering the distal end of the body and selectively removable from the distal end. The present invention also includes methods for using such a cannula for separating tissue to form an elongated cavity along the course of a small blood vessel and subsequently harvesting the blood vessel, or using the blood vessel as an in-situ graft.

Figure 1:
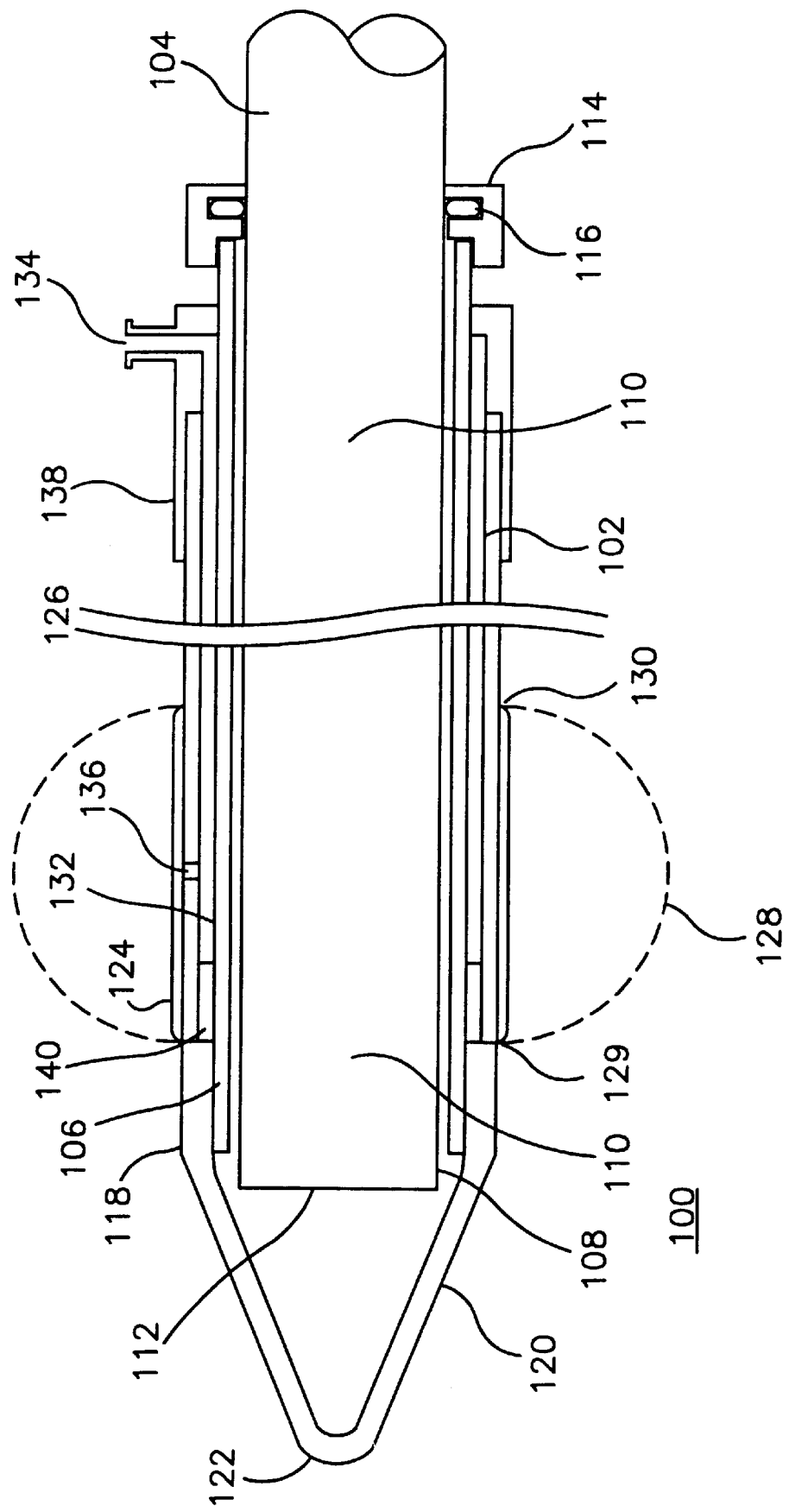
FIG. 1 is a partial, longitudinal cross-sectional view of a cannula of the present invention illustrating the profile of a tissue separating member affixed thereto.

FIG. 1 shows an embodiment of the cannula 100 of the present invention. The cannula 100 includes a tubular body 102 having a proximal end 104 and a distal end 106. At least one lumen 108 extends the length of the body 102. Disposed in the lumen 108 is an endoscope 110 having a lighted, viewing end 112 near the distal end 106 of the body. The other end of the cannula 100 has a proximal end cap 114 and an elastomeric washer 116 that provides a pressure-sealed, sliding fit with the endoscope 110.

The cannula 100 also includes a transparent, tissue separating member or blunt tip 118 substantially covering the distal end 106 of the body. The tissue separating member 118 has a tapered section 120 which angles toward a blunt, tissue-separating tip 122 distal to the distal end 106 of the tubular body. The shape of the tissue separating member 118 allows atraumatic dissection of a cavity with sufficient control and maneuverability to prevent tearing or puncturing of the nearby vessel. Typically, the tip 122 has an outer radius of curvature of about 0.030" to about 0.100", and preferably of about 0.045". The length of the tapered section 120 of the tip is approximately 0.500" in length. The tapered shape and blunt tip of the tissue separating member 118 thus allows deflection of branch vessels to the side of the cannula 100 without their avulsion, upon forward advancement of the cannula 100 with reduced requirement of applied axial force to advance the cannula and tip through tissue being dissected.

Figure 8A:
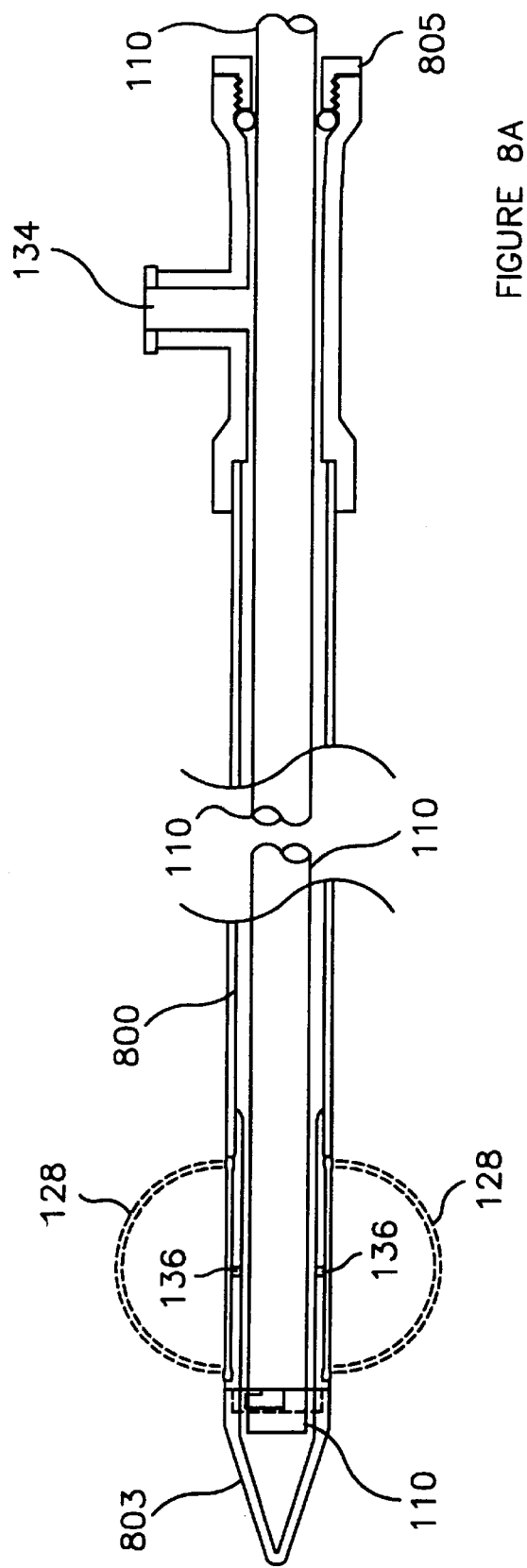
FIGS. 8A AND 8B are partial side sectional views showing alternative embodiments of detachable blunt tips positioned at the distal end of the cannula.
Figure 8B:
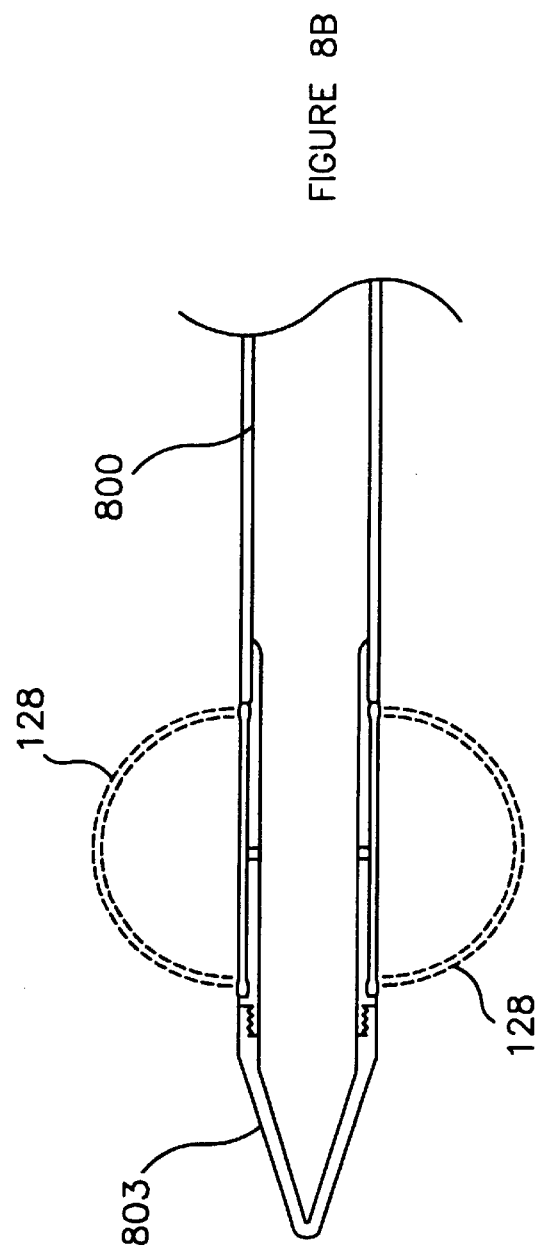

In tapers of uniform wall thickness with a rounded inner surface near the apex, it has been found that a small circular spot of distortion exists in the center of the visual field of the endoscope, equivalent to the diameter of the rounded taper tip. This distortion may be substantially eliminated by forming the transparent taper with an inner profile that ends in a sharp point, or apex, while maintaining the outer profile as a rounded tip with approximately a 0.045" radius. Undistorted visual imaging through such tip thus allows the surgeon to track down the vessel, identify side branches, and guide the device past the side branches. An optimal taper length of approximately 0.5" facilitates cannula manipulation around side branches, and the preferred configuration of the tapered tip is illustrated in FIGS. 8A and 8B.

Figure 2:
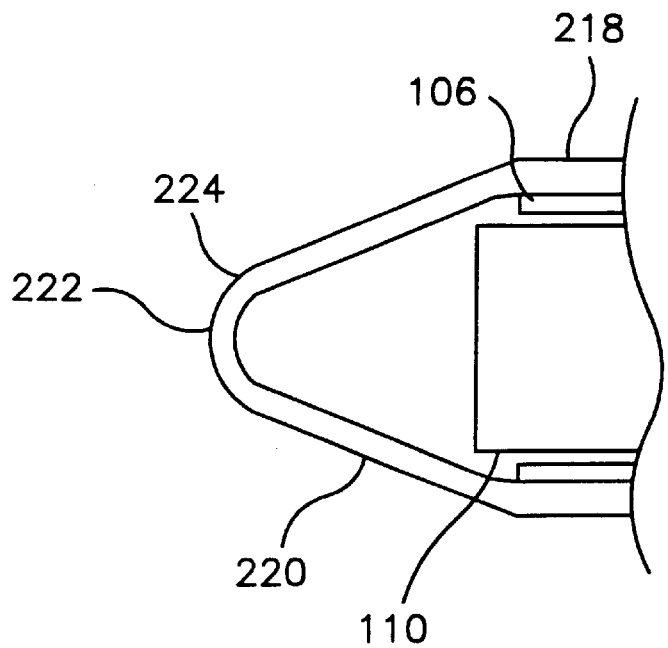
FIG. 2 is an isolated, cross-sectional view of another embodiment of the tissue separating member having a blunt spherical tip with a straight tapered section suitable for use with the cannula of the present invention.

Alternative embodiments of the present invention include other shapes for the tissue separating member 118 which provide the necessary control and atraumatic dissection. FIG. 2 illustrates another embodiment of a tissue separating member 218 which substantially covers the distal end 106 of the cannula and provides a transparent shield for the endoscope 110. The tissue separating member 218 includes a tapered section 220 integrally formed with a more blunt, spherical section 224 at the distal tip 222 of the tissue separating member.

Figure 3:
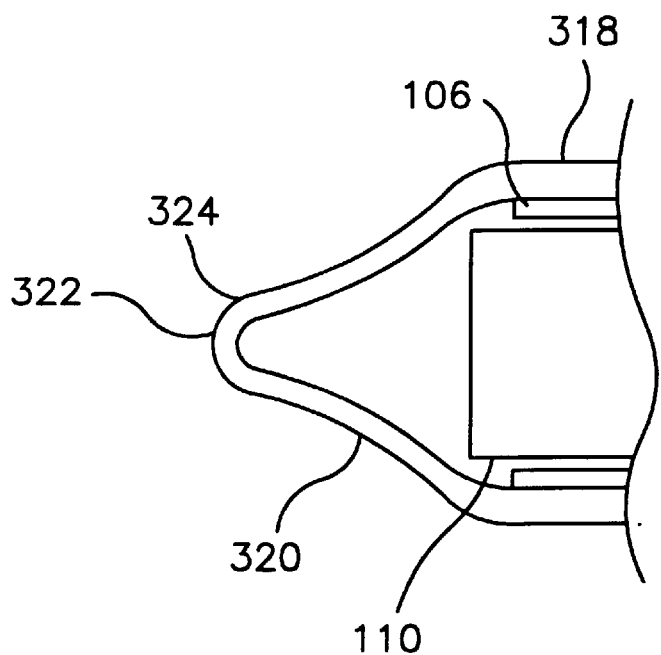
FIG. 3 is an isolated, cross-sectional view of another embodiment of the tissue separating member having a blunt tip with a curved tapered section suitable for use with the cannula of the present invention.

FIG. 3 illustrates another embodiment of a tissue separating member 318 which substantially covers the distal end 106 of the cannula and provides a transparent shield for the endoscope 110. The tissue separating member 318 includes a curved tapered section 320 integrally formed with a blunt section 324 at the distal tip 322 to form a duck-bill shape. The curved tapered section 320 can have convex or concave shape.

Figure 4:
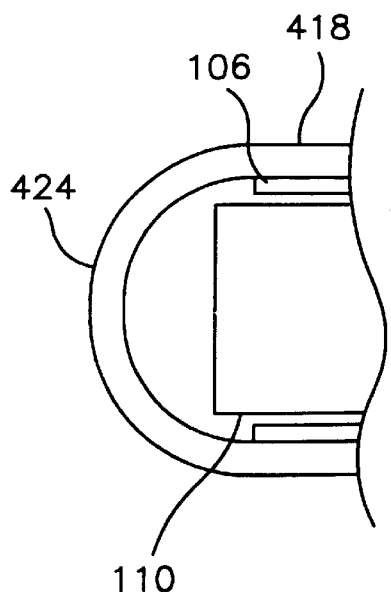
FIG. 4 is an isolated, cross-sectional view of another embodiment of the tissue separating member having a hemispherical shape suitable for use with the cannula of the present invention.

FIG. 4 illustrates another embodiment of a tissue separating member 418 which substantially covers the distal end 106 of the cannula and provides a transparent shield for the endoscope 110. The tissue separating member 418 has a hemispherical shape 424 covering the distal end 106.

Preferably, the tissue separating members 118, 218 have an overall length of about 0.5 inches and a uniform wall thickness of about 0.06 inches along the entire surface to allow visualization by the endoscope without distortion of the image that would result if a section of the wall is thickened or otherwise forms a lens. The wall thickness of the tissue separating member may be contoured to form a lens for special applications that require a magnified or otherwise distorted image, e.g. asymmetric, fish-eyed image, or the like, transmitted by the endoscope. Suitable materials for making the tissue separating member or blunt tip include polycarbonate and any material which is sufficiently strong to separate tissue and sufficiently transparent to allow visualization by the endoscope. As illustrated in FIGS. 8A, 8B, 9A, and 9B, the tissue separating member or blunt tip may be attached by threads or bayonet-type twist lock to the cannula for selective removal during procedures later described herein.

Referring again to FIG. 1, the cannula 100 preferably includes a balloon 124 located at the distal end 106 on the exterior wall 126 of the cannula. The balloon 124 may be elastic or inelastic, although an elastomeric balloon is preferred because it achieves a smaller, smoother outer profile. Fully inflated (as shown in phantom 128 in FIGS. 1, 8A, and 8B), the diameter of the balloon 124 is about 3 cm. Preferably, a sleeve type of balloon 124 has both the distal end 129 and proximal end 130 of the balloon secured to the exterior wall 126 of the cannula.

The balloon 124 is selectively inflated by supplying thereto via another lumen 132 a pressurized fluid, such as a gas or liquid, from an inflation port 134 to a hole 136 in the exterior wall 126 of the cannula between the proximal and distal ends 129, 130 of the balloon to communicate with the interior thereof. A plunger device, such as a manually-operated syringe, is suitable for connecting at the inflation port 134 to control the inflation of the balloon 124. The lumen 132 is formed as another tubular body 138 in a concentric arrangement with the body 102 to form a space 140 between the two bodies. Another embodiment suitable of the present invention may include two lumens 108, 132 in a side-by-side arrangement. Additional lumens can be added in similar manner to provide other functions such as irrigation and aspiration in known manner.

The present invention is illustrated using a sleeve type of balloon with the cannula 100. Other balloon types are suitable for use with the present invention such as, and not limited to, using an invertable balloon positioned in a separate lumen in the cannula to assist in separating the tissue when inflated.

The cannula 100 may be manufactured from a variety of bioinert, substantially inelastic materials, such as stainless steel, polyethylene, polyurethane, polyvinyl chloride, polyimide plastic, and the like that preferably have a tensile strength of at least 10,000 psi. Preferably, each lumen of the cannula 100 has a wall thickness of between about 0.005 inch and 0.010 inch.

The endoscope 110 has an outer diameter of approximately 5.0 mm and an endoscope may be permanently built into the cannula 100, or may be a separate device that is advanced through the endoscope lumen 108, for example, through a sliding gas-tight seal 805 configured as shown in FIG. 8A in conventional manner. The endoscope 110 is positioned within the lumen 108 with the tip in correct position to allow unimpeded visualization through the transparent blunt tip of the surrounding tissue and vessel outside of the cannula 100. A preferred endoscope 110 having a tubular diameter of about 5.0 mm is commercially available from Solos Endoscopy, Inc., at Norcross, Ga., although other commercially-available endoscopes 110 as small as 1.00 to 1.75 mm in diameter may also be used.

Figures 5, 6:
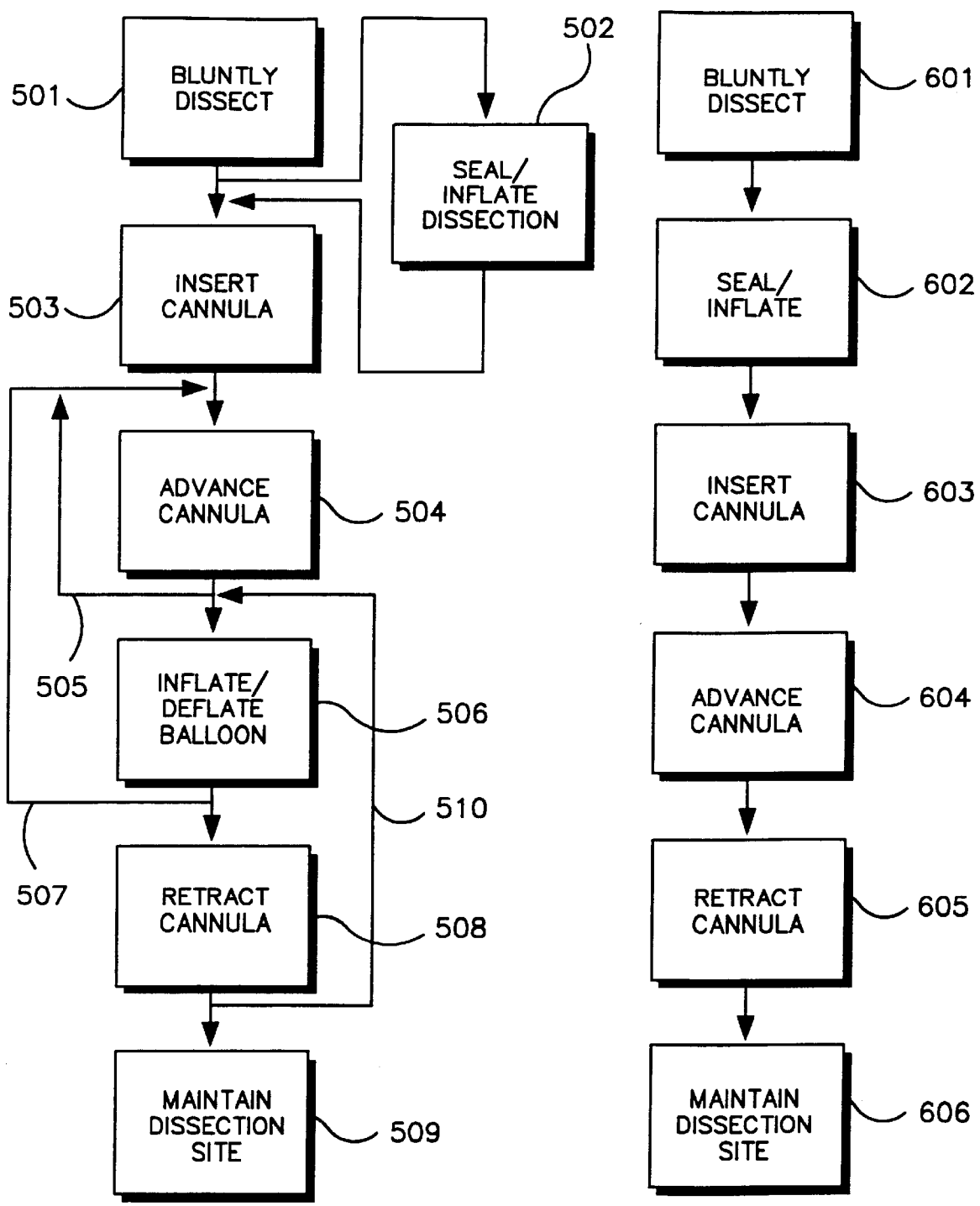
FIG. 5 is a flowchart of one embodiment of the method of separating tissue using the cannula of the present invention.
FIG. 6 is a flowchart of another embodiment of the method of the separating tissue.

Methods for bluntly dissecting an elongated cavity using the cannula of the present invention are shown in the flow diagrams of FIGS. 5 and 6. Although the blunt dissection of an elongated cavity along the course of a vessel is specifically described, the present invention is generally suitable for separating any tissue. For example, the cannula may be used to track along the median nerve from an incision at the patient's wrist, forming a cavity for surgical treatment of carpal tunnel syndrome. The cannula allows visualization and tracking of the median nerve, preventing the injury to the nerve which may occur if blind advancement of a balloon cannula were used. Alternatively, the cannula of the present invention may also be used to dissect a cavity adjacent the mammary artery in the manner as later described herein.

The method illustrated in the flow diagram of FIG. 5 includes the steps of incising the skin and bluntly dissecting 501 through the subcutaneous tissue to the level of the selected vessel or nerve. Blunt dissection is performed to separate the vessel from adjacent tissue for a length of approximately 1 to 2 cm. The blunt dissection may be performed with a pair of curved Metzenbaum scissors, using the tips of the scissors to cut and bluntly spread tissue in a plane between the vessel and the adjacent tissue.

Preferably, a blunt tip balloon cannula is introduced into the space between the vessel and the overlying tissue. The balloon is then inflated to form a gastight seal which seals 502 the dissection. A gas such as carbon dioxide is infused under pressure via another lumen in the cannula having an external opening positioned distal to the balloon. The natural perivascular plane around the vessel is expanded by the injected gas, forming a tract along the course of the vessel. For a superficial vessel such as the saphenous vein, the expanded tract is visible on the surface of the skin. The interior of the expanded tract is not cleanly open but rather, includes gossamer-like strands of connective tissue and fat, preventing unobstructed visualization and making hazardous the passage of an endoscope along the tract adjacent to the vessel. If a conventional endoscope is pushed into this connective tissue in an attempt to form a cavity adjacent to the vessel, the view through the conventional endoscope is blurred by the tissue that contacts the viewing end of the conventional endoscope. A blurred view through the conventional endoscope increases the potential for side branch avulsion during blunt dissection of the perivascular tunnel.

The cannula 100 is inserted 503 into this dissected space. With the fiberoptic endoscope 110 continuously visualizing down the course of the vessel, the cannula 100 separates the tissue by advancing forward 504, probing between the vessel and the adjacent gossamer perivascular tissue in the plane initiated by blunt dissection. The transparent, tissue separating member 118 allows the endoscope 110 to clearly visualize a segment of the vessel at least equivalent to the length of the tapered section 120.

If the blunt dissection along the course of the vessel is not sufficient to advance the balloon 124 therein, the method returns 505 to the step of advancing the cannula 504 forward to continue the separation of tissue along the course of the vessel. When a cavity of sufficient length has been formed by the cannula 100, the balloon 124 is successively inflated and deflated 506 to enlarge the cavity to about 3 cm in diameter.

The method returns 507 to the step of separating the tissue by advancing the cannula 504 and the step of selectively inflating and deflating 506 the balloon 124, as described above. Successive application of these steps forms a cavity along the entire length of the vessel. Once the elongated cavity is complete, the cannula 100 is completely retracted 508 from the elongated cavity.

The elongated cavity site is then maintained 509 in expanded form in accordance with the method of the present invention. Following use of the cannula 100 to form an elongated cavity along the course of a vessel, the cavity must be supported to allow procedures to be performed on the vessel, such as vessel dissection, grafting of the vessel, or vessel harvesting. A blunt tip trocar may be used to seal the entrance incision and allow gas insufflation to maintain the cavity in expanded form. One blunt-tip balloon trocar suitable for use herein is presently marketed by Origin Medsystems, Inc. of Menlo Park, Calif.

Another method of maintaining the cavity in expanded form includes making an incision at the distal extent of the dissected cavity, and inserting a double rod system through the cavity. The double rods are suspended via a laparoscopic mechanical lifting device to maintain the cavity. This system allows instruments to be advanced into the cavity via simple incisions, without the requirement for trocars with gas sealing valves, as is the case with gas insufflation.

Alternatively, an inflatable structural balloon or mechanical structure may be used to support the dissected cavity. For example, the cavity may be maintained by mechanical retraction or by a mechanical finger-like retractor attached to a powered lifting arm plus a separate flat balloon retractor used to displace the side wall of the cavity. The endoscope 110 may be introduced behind. the legs of the finger-like retractor that connect to the mechanical lifting arm.

The vessel is completely dissected within the formed cavity, using laparoscopic instruments such as graspers, scissors, hooks, and blunt probes. Side branches to the vessel may be ligated using suture ties, clipped using titanium vessel clips, cauterized using electrocautery, or a combination of these procedures. The dissected vessel is removed from the cavity for possible use as a conduit for an arterial bypass procedure, or the vessel may be left in place to be used as an in-situ bypass graft.

In an alternate embodiment, the method of the present invention forms a small diameter cavity, about 7 mm, along the entire length of the vessel before the cavity is then enlarged. As illustrated in FIG. 5, the steps of making a blunt dissection 501, sealing and inflating the dissection 502, inserting 503 the dissection cannula 100 and successively separating the tissue by advancing 504 the cannula 100 are performed as described above. The alternate method, however, continues advancing 504 the dissection cannula until the entire length of the elongated cavity is bluntly dissected to the small diameter of about 7 mm.

Only after the entire length of the elongated cavity has been bluntly dissected does the alternate method include the step of inflating and deflating 506 the balloon 124 of the cannula to increase the diameter of the distal end of the elongated cavity to about 3 cm. The dissection cannula 100 is then retracted 508 partially by about the length of the balloon 124. The alternate method then returns 510 to the steps of inflating and deflating 506 the balloon 124. The cannula 100 is again retracted 508 partially and the method returns 510 to repeating the above steps until the entire length of the elongated cavity has been enlarged to the diameter of the inflated balloon 124 which is typically about 3 cm.

An alternate method involves making an incision down to the vessel. Blunt dissection of the vessel from the adjacent tissue is performed for a 3–4 cm length. A blunt tip trocar is placed in the incision, and gas insufflation is initiated.

The cannula 100 is inserted through the blunt tip trocar, and blunt dissection using the balloon 124 is performed under the presence of gas insufflation in the cavity. This technique provides a larger cavity for visualization during separation of the tissue, since gas insufflation is used from the onset of blunt dissection. However, a gas sealing blunt tip trocar is required. If vessel dissection without gas insufflation is conducted, and a double rod system is used to maintain the cavity, then the use of a blunt tip trocar may be avoided.

Another method of the present invention forms a small diameter cavity along the entire length of the vessel. The cavity is enlarged only by the initial inflation at the blunt dissection site. As illustrated in FIG. 6, the steps of making a blunt dissection 601, sealing and inflating the dissection 602, inserting 603 the cannula 100, and successively separating the tissue by advancing 604 the cannula 100 are performed as described above. The cannula advances 604 until the entire length of the elongated cavity is bluntly dissected and expanded only by the inflating gas of the prior step 602. The cannula 100 is then retracted 605 entirely from the elongated cavity. The dissection site. is maintained 606 in expanded form as described above.

The present invention includes methods particularly useful for harvesting vein. In one method, an incision is made near the ankle, and the cannula is passed along the sophenous vein up to the knee, or near the knee. Following balloon inflation to enlarge this segment, an incision is made into the dilated cavity near its endpoint at the knee. The incision at the knee is the approximate mid-point of the saphenous vein between the ankle and the groin. The vein is isolated and the side branches ligated in this segment between the ankle and the knee to harvest and remove this segment.

The segment from the knee to the groin is then harvested. The cannula may be passed from the same knee incision used for harvesting the vein from the lower leg, or a separate incision down to the vein may be made slightly above the knee. Use of a separate incision may be useful if the vein is overly curved or tortuous as it passes around the knee. The cannula is advanced toward the groin, the balloon is inflated to dilate the cavity, an incision is made into the dilated cavity at its groin end, and the portion of the saphenous vein residing in the thigh is harvested.

As an alternate method for saphenous vein harvesting, the initial incision may be made at the knee. The cannula is passed successively in both directions, toward the ankle and toward the groin, from the same incision. Then additional incisions are made at the ankle and at the groin to allow harvesting of the entire length of the saphenous vein. The vein may be removed as a single strand, or it may be cut at the knee and removed as two strands.

In some anatomic regions, it may be difficult to advance a rigid, straight tissue separation device along the course of a vessel. For example and referring to FIG. 7, if the saphenous vein 700 is harvested by passing the cannula 702 from an incision 712 just above the ankle, the presence of the medial malleolus 704 and the foot 706 may prevent an otherwise rigid cannula from being angled upwards oir sideways to follow the vein 700.

Figure 7:
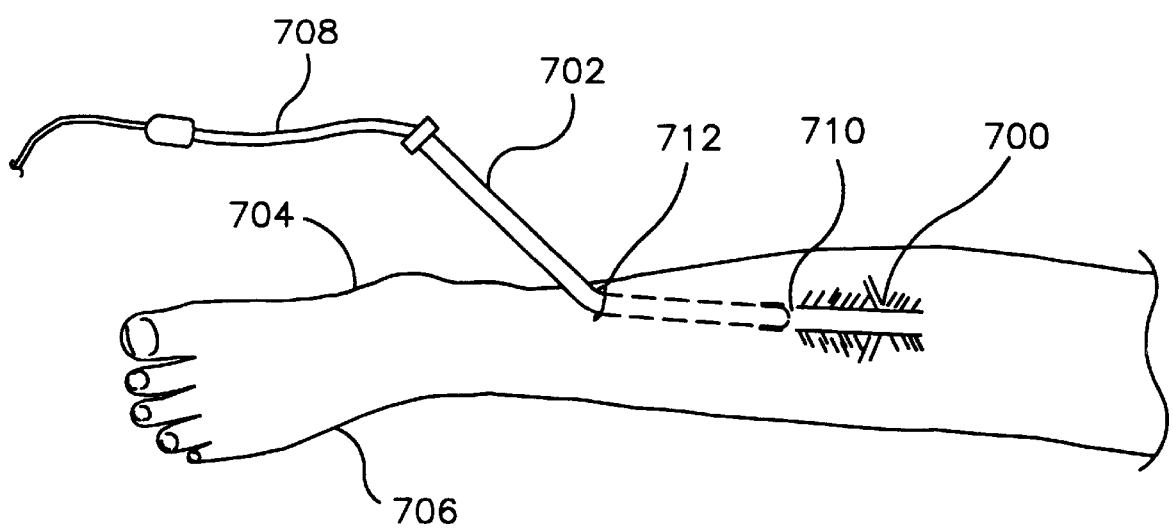
FIG. 7 is a partial side view of a patient's leg with the advancement of a flexible cannula of the present invention through an incision.

For such obstructed situations, the cannula 702 may be formed with a body which is flexible or otherwise malleable, or is rigid with a pre-determined gradual arc, as shown in FIG. 7. The endoscope 708 that is inserted into the cannula 702 up to the tissue separating member 710 must also be flexible to facilitate shaping the flexible body within the curved cannula. Such conventional flexible fiberoptic endoscopes are commercially available for use in gastrointestinal endoscopy.

In other embodiments of the method, and of the apparatus illustrated in FIGS. 8A and 8B, the tapered and transparent tip 803 of the cannula 800 may be removably attached to the body of the cannula. At the cannula insertion site, a blunt tip balloon trocar (for example, as commercially available from Origin Medsystems, Inc.) is placed to seal an incision and allow insufflation into the space to be dissected by the cannula 800 which is advanced through the blunt tip trocar along the course of the vessel. The balloon on the cannula is selectively inflated to dissect a perivascular cavity. Following dissection of the cavity along the vessel, a counterincision is made at the far end of the cavity to place a second blunt tip balloon trocar and allow introduction of dissection instruments. The tip of the cannula is advanced out of the body through the counterincision and the tapered tip 803 is detached, leaving the cannula body in the dissected cavity. The endoscope resides inside the cannula body, and the endoscope/cannula body is advanced as a single unit inside the working cavity to isolate and harvest the vessel.

The detachable tip 803 may be attached to the cannula body 800 using a threaded connection between the tip and the distal end of the cannula body, or a bayonet-type of fitting my be used to lock the tip onto the cannula, with a slot in the tip engaging a pin on the end of the cannula body.

The cannula of this embodiment with a detachable tip 803 has the advantages compared with the embodiment of the cannula described with reference to FIG. 1 that the 5 mm diameter endoscope used with the cannula often does not have sufficient rigidity to allow it to be directed along the dissected working cavity for unobstructed visualization. For example, in the lower leg, the curvature of the calf muscle impedes visualization along the surgical cavity, and the endoscope must deflect muscle tissue to allow it to view down the bore of the cavity. Flexion of the endoscope which is about 45 cm long and about 5 mm diameter may prevent successful visualization. The cannula which surrounds the endoscope according to the present invention has an 8 mm outer diameter, and this larger diameter imparts rigidity to the endoscope/cannula system. The cannula body may be constructed of stainless steel for additional rigidity.

Also, the ability to remove the tapered tip 803 via an incision at the opposite end of the cavity results in a decreased number of passes of the cannula and endoscope up and down the length of the cavity. This adds to the convenience of the procedure, and decreases the potential for vessel injury by decreasing the number of full length passes required through the dissected cavity.

Referring now to FIGS. 9A and 9B, retracted and dissembled configurations of another embodiment of the cannula 900 of the present invention are illustrated. Specifically, the outer body of the cannula 900 includes a sleeve-type balloon 901 secured to the body at proximal and distal ends thereof, as illustrated in FIGS. 8A and 8B, for selective inflation via a lumen 1010 within the body that communicates therewith, as illustrated in the sectional view of FIG. 10.

At the distal end of the body of the cannula 900, a detachable, transparent blunt tip 903 is shown in FIG. 9A retracted onto the distal end of the cannula body, and is shown in FIG. 9B mounted on push rod 906 and extended beyond the distal end of the cannula body 900 to expose the viewing end 905 of an endoscope, and a crescent-shaped dissection probe 907. The probe 907 is mounted on shaft 909 to facilitate selective manipulation of the dissection probe 907 within the field of view of the endoscope 905. As shown in FIG. 10, the push rod 906 may be non-circular within a mating non-circular lumen to retain the blunt-tip 83 in axial alignment as it is selectively extended and retracted relative to the distal end of the cannula body 900. Also as shown in FIG. 10, the shaft 909 for supporting the dissection probe 907 may be circular or cylindrical to facilitate both longitudinal and rotational positioning of the dissection probe 907 via corresponding manipulations of the shaft 909 at the proximal end of the cannula body 900. Alternatively, the shafts 906 and 909 may reside in slots of suitable sectional shapes along the outer surface of the cannula body 900, with an encircling sheath of heat-shrinkable PET plastic, or other bioinert plastic, to retain the shafts 906, 909 in captivated orientation along the cannula body 900.

The dissection probe 907 has leading and trailing edges thereof to facilitate selective dissection of strands of connective tissue and lateral branch vessels along the saphenous vein, or other vessel, to be harvested. The blunt tip 903 may thus be selectively extended beyond the cannula body 903 (or the cannula body 900 may be retracted relative to the tip 903) to expose the dissection probe 907 at a selected location along a dissected cavity adjacent a vessel being harvested. Selective translational and rotational manipulations may be achieved via similar manipulations of the shaft 909 at the proximal end thereof to dissect connective tissues and lateral branch vessels along the course of the vessel being harvested. The dissection probe 907 and the blunt tip 903 may then be retracted into axial alignment with the cannula body 900, as shown in the retracted configuration of FIG. 9A. Surgical procedures involving the cannula 900 of FIG. 9A are described later herein with reference to the flow chart of FIG. 16.

Referring to the side and sectional views of FIGS. 11A, 11B, and 11C, the dissection probe may be formed in separate, spiral-like segments 1101, 1103 that are axially spaced along the supporting shaft 909, for example, in the illustrated configuration, to provide greater convenience in selectively by-passing or dissecting connective tissue and lateral branch vessels along the course of a vessel being harvested. Thus, as shown in FIGS. 11D and 11E, the dissection probe 907 (or 1101 and 1103) may be orbited about the axis of shaft 909, and the cannula body 900 may be rotated on its longitudinal axis to facilitate the dissection of the vessel away from connecting tissue, and the traversal of side-branch vessels.

Figure 12A:
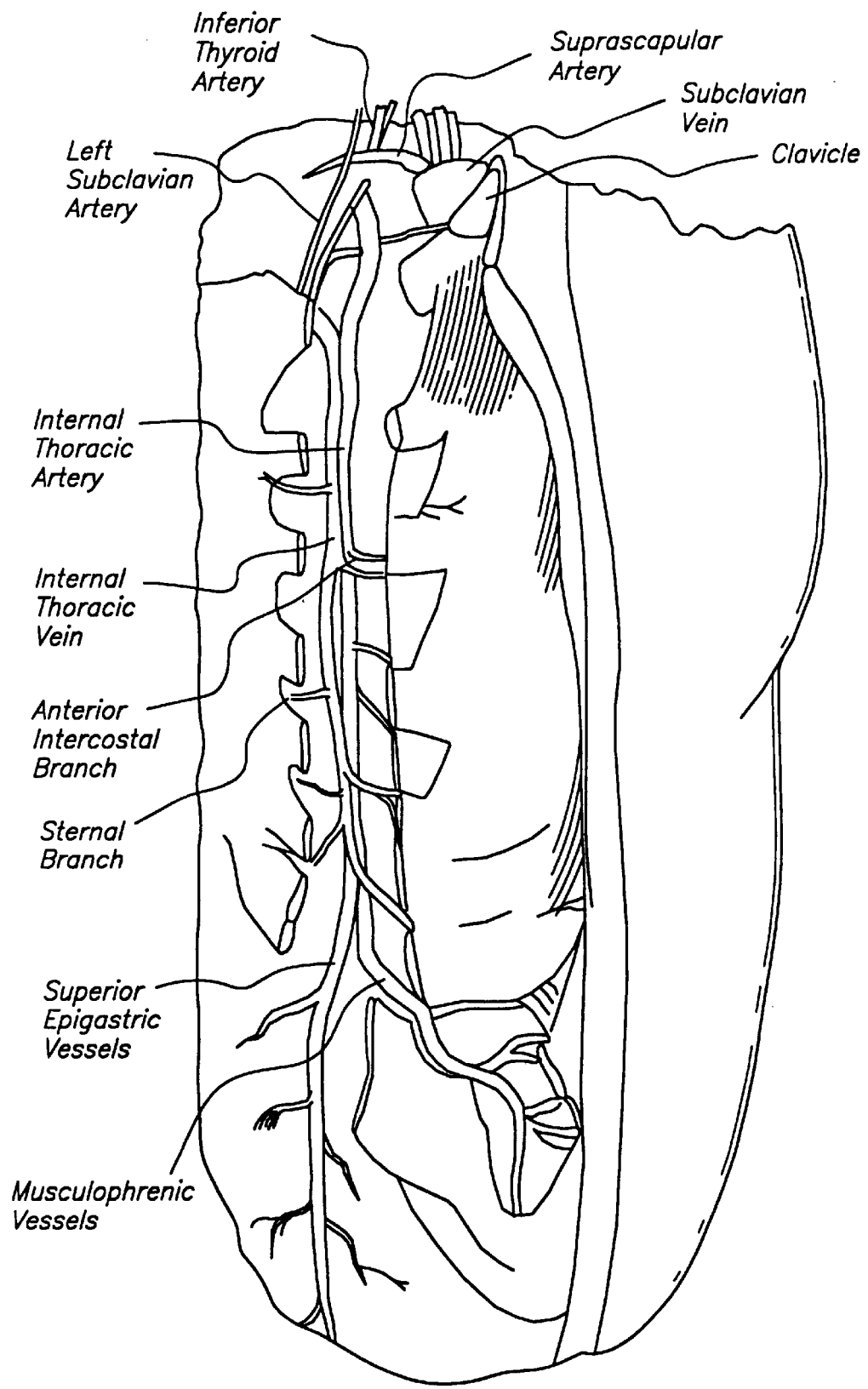
FIGS. 12A, 12B and 12C are, respectively, simplified anatomical side sectional and front sectional views of the human body.
Figure 12B:
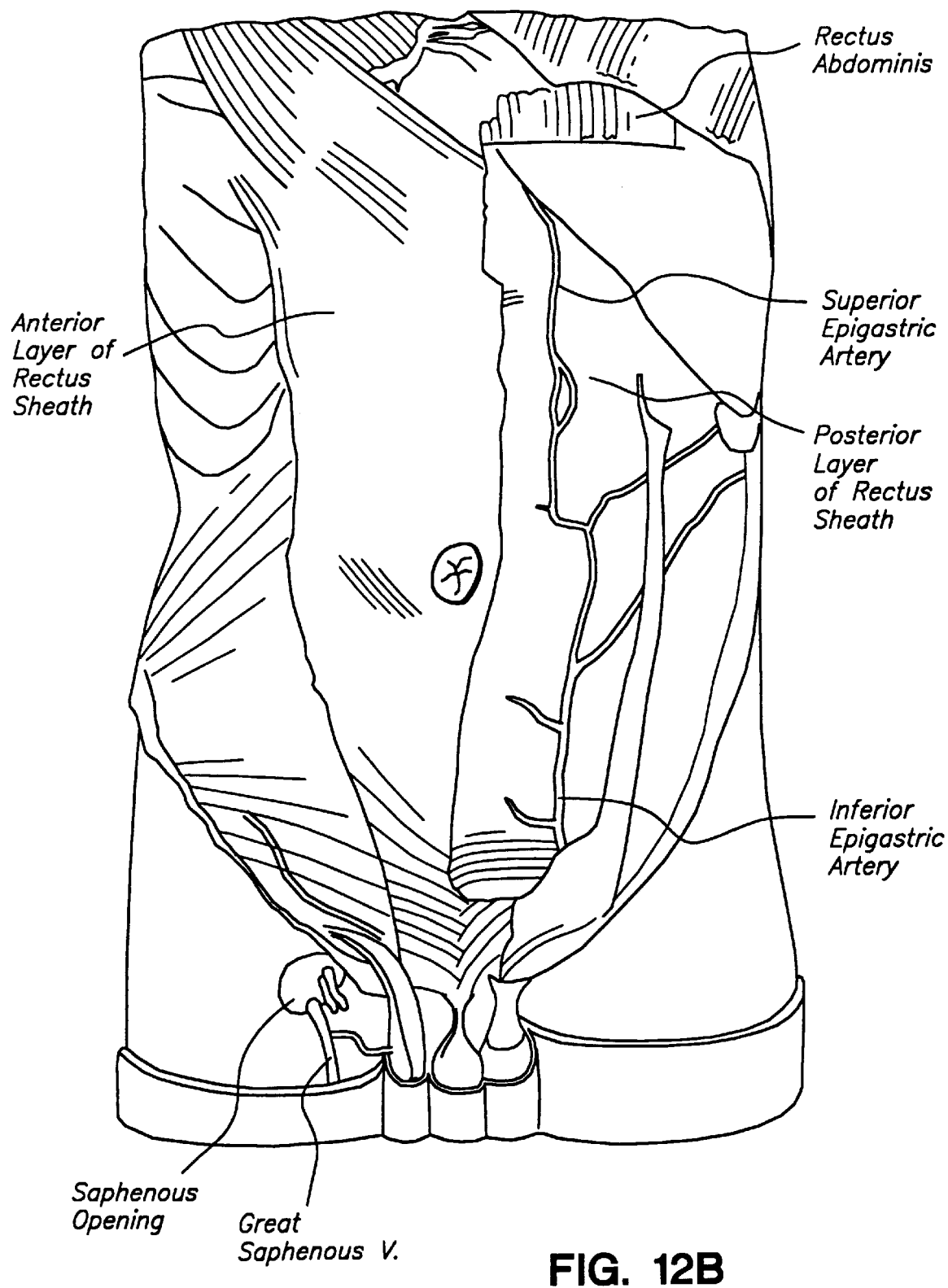

Referring now to FIGS. 12A and 12B, the simplified side and frontal illustrations of the human anatomy disclose another operating environment for the apparatus and method of the present invention, for example, in preparing the internal mammary artery for coronary artery bypass. Specifically, the combined blunt tip cannula and dissection probe of the present invention permits a working cavity to be formed along a vessel, and the vessel to be dissected and isolated, or otherwise manipulated as later described herein, via a single incision. This decreases the number of incisions required to harvest a vessel. The cannula and dissection probe of the present invention facilitate harvesting the internal mammary artery in the chest wall to enable its use as a coronary artery bypass graft. The internal mammary artery may be harvested via a single subxiphoid incision, with the rectus muscle bluntly dissected to expose the superior epigastric artery. The cannula tracks along the superior epigastric artery which leads directly to the internal mammary artery that lies behind the ribs lateral to the sternum. The internal mammary artery is dissected substantially in the manner as previously described up to its origin at the subclavian artery. Its side branches are clipped and transected, and distally, it is transected to yield a free end which is anastomosed to the coronary artery to complete the bypass.

Figure 12C:
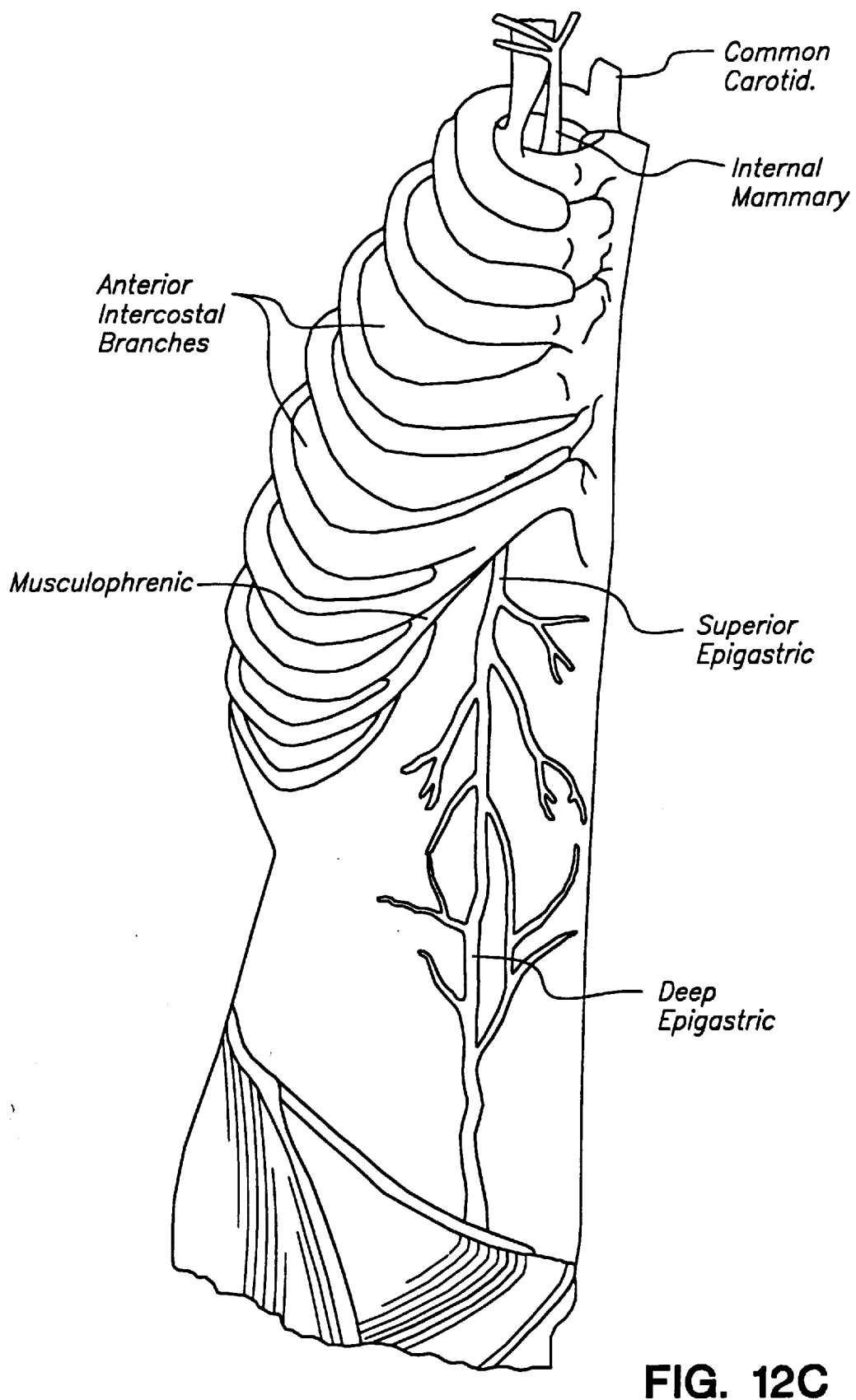

As illustrated in FIGS. 12A, 12B and 12C, the internal mammary artery (also known as the internal thoracic artery) runs internal to the costal cartilages, lateral to the sternum, descending to the interval between the sixth and seventh cartilages where it bifurcates into the superior epigastric artery and the musculophrenic artery. The superior epigastric artery lies within the rectus sheath. In its superior portion, it lies behind the rectus abdominis muscle. The superior epigastric artery eventually anastomoses with the inferior epigastric artery.

Since the superior epigastric artery lies in the abdominal wall within the rectus sheath, it may be easily found, for example, using Doppler ultrasound, and isolated via incision of the skin and blunt spreading of the rectus abdominis muscle overlying the artery. The blunt tip, visual balloon dissection cannula previously described herein may be placed next to the isolated section of superior epigastric artery, and passed superiorly, following the course of the superior epigastric artery to its junction with the internal mammary artery. An endoscopic working cavity may be formed along the length of the internal mammary artery in the manner previously described herein, allowing side branch identification and interruption, and using vessel clips or bipolar electrocautery closure followed by scissor transection. The dissected portion of the internal mammary artery may then be used to revascularize diseased coronary arteries, facilitated by the availability of the endoscopic working cavity thus formed along the internal mammary artery.

This abdominal approach to internal mammary artery dissection is preferable to a supraclavicular approach or an intercostal approach since the supraclavicular approach is impeded by the presence of the subclavian artery and the aortic arch, and dissection risks trauma to these vessels. In contrast, the intercostal approach gives limited exposure, unless rib spreaders are used, and only a small portion of the internal mammary artery is accessible from the side. The abdominal approach described herein thus allows the entire length of the internal mammary artery to be exposed. By initiating the dissection at the level of the superior epigastric artery, no vascular or bony structures are present to impede the passage of the dissection cannula of the present invention, thereby resulting in a safer approach to the internal mammary artery.

Figure 15:
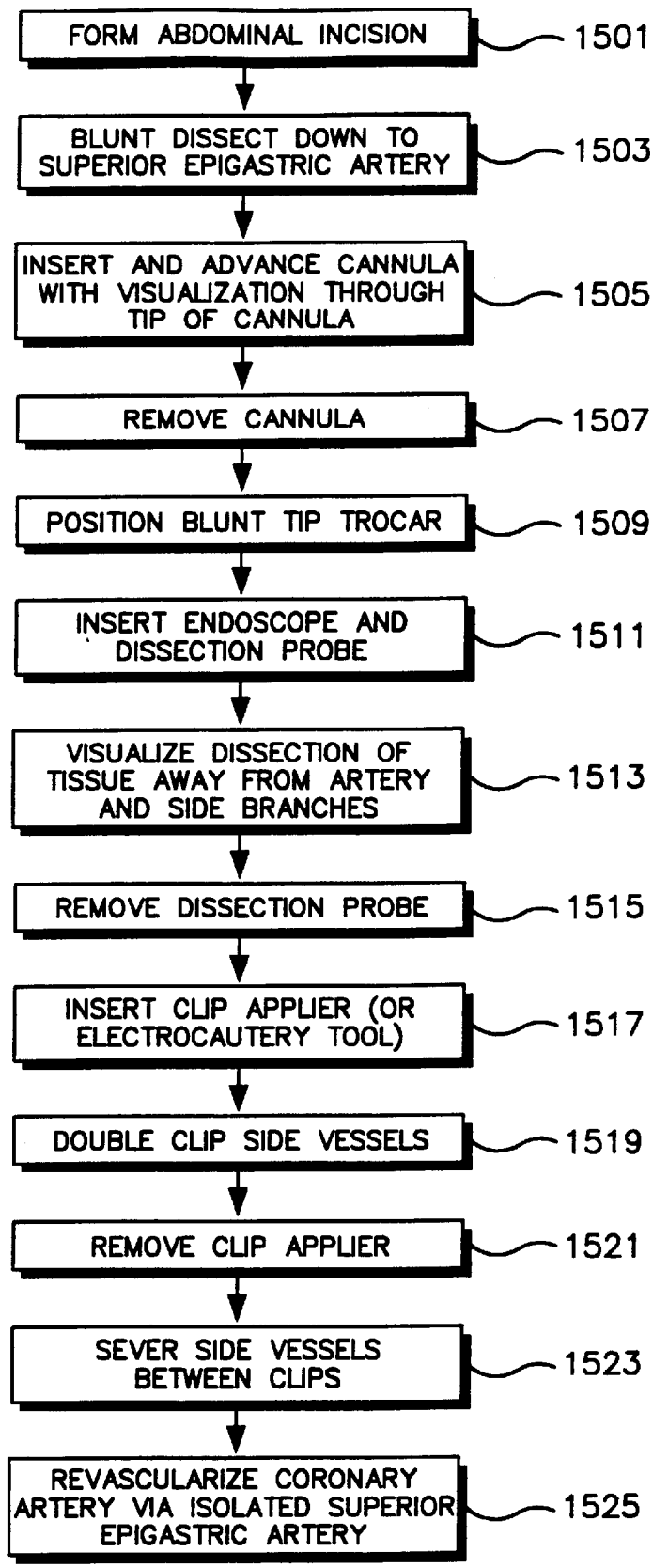
FIG. 15 is a flow chart of an artery isolating procedure according to the present invention.

Specifically, with reference to the flow chart of FIG. 15, the method of creating a working space along the superior epigastric artery according to the present invention includes forming an incision 1501 of the skin and blunt dissection 1503 and spreading of the rectus abdominus muscle overlying the artery. The balloon cannula as illustrated in FIGS. 1, or 8A, 8B, or 9A, 9B, 13A, 13B is inserted in the bluntly dissected cavity next to the isolated section of the superior epigastric artery. The cannula is advanced 1505 along the course of the superior epigastric artery and the internal mammary artery by the iterative sequence of advancing the cannula, visualizing dissection of tissue through the transparent tip until resistance to tissue penetration is felt. The balloon is inflated to expand the cavity around the cannula adjacent the artery, and then deflated, and the cannula is again advanced, and retracted and diverted and advanced as required to properly track the course of the vessel substantially to its junction with the subclavian artery. The tunnel or cavity thus formed along the artery facilitates side branch identifications for subsequent operative procedures, and in one embodiment of the process invention the cannula may be completely removed 1507 from the working cavity thus formed by successively inflating and deflating the balloon to establish an adequate working cavity as the cannula is completely withdrawn therefrom.

Next, the artery may be dissected from the cavity wall by placing 1509 a blunt tip trocar in the working cavity at the abdominal incision, and the associated balloon is then inflated. The cannula of the present invention including the dissection probe and an endoscope positioned 1511 within a lumen of the cannula is positioned in the working cavity through a gas tight port of the trocar, with the dissection probe positioned about the artery. The dissection probe is now translated and rotated 1513, as illustrated in FIGS. 11D and 11E to free the artery from connective tissue. The axial opening 908 in the perimeter of the dissection probe facilitates passing over lateral branch vessels encountered along the course of the artery being isolated. When the artery and side branches are completely free of connecting tissue, the cannula with endoscope and dissection probe is removed 1515 from the working cavity.

Figure 14:
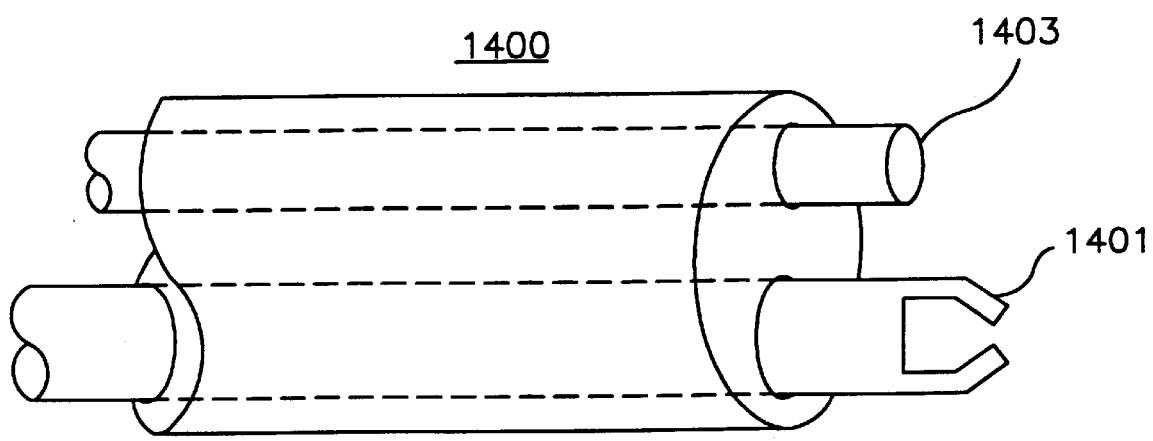
FIG. 14 is a partial pictorial view of a viewing, multiple-clip applier for use in the method of the present invention.

Thereafter, a viewing, multiple-clip applier, as illustrated in FIG. 14, including a clip applier 1401 and an endoscope 1403, and having a circular cross section may be inserted 1517 through the trocar port for placing two surgical clips on each side branch of the isolated artery 1519, spaced sufficiently to divide the branch vessel therebetween. After all side-branch vessels are clipped in this manner, the viewing, multiple-clip applier is completely removed 1521. Alternatively, a two-port, trocar gas seal may be attached to the blunt tip trocar and an endoscope may be inserted through one port with a clip applier or electrocauterizer inserted through the other port for clipping or otherwise occluding the side-branch vessels. The two-port seal for the blunt tip trocar facilitates removal of only the clip applier and replacement thereof by scissor blades that can be manipulated proximally to cut and divide 1523 each of the side branch vessels between the clips that were previously placed or through electrocauterized segment that was prepared while viewing through the endoscope 1403. Thereafter, the scissor blades may be removed, and the internal mammary artery thus isolated may then be used to revascularize diseased coronary arteries 1525, for example, by grafting a transsected free end of the isolated internal mammary artery to the left anterior descending coronary artery downstream of a significant stenotic occlusion.

Figure 13A:
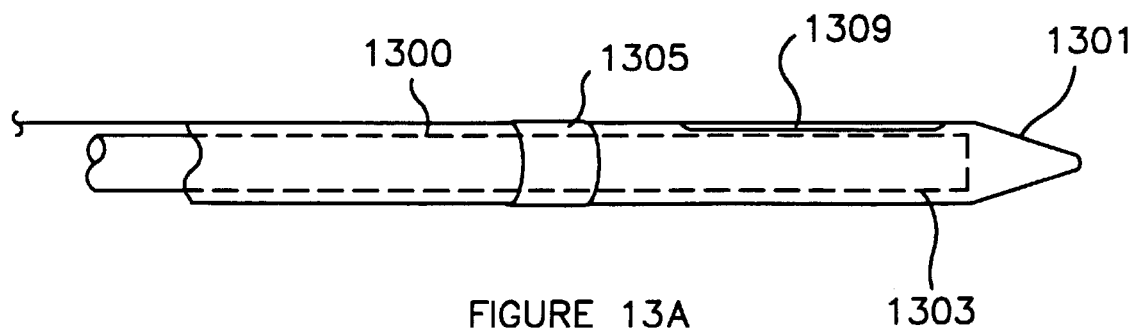
FIGS. 13A and 13B are side views illustrating, respectively, retracted and extended configurations of another embodiment of the tissue separating cannula of the present invention.
Figure 13B:
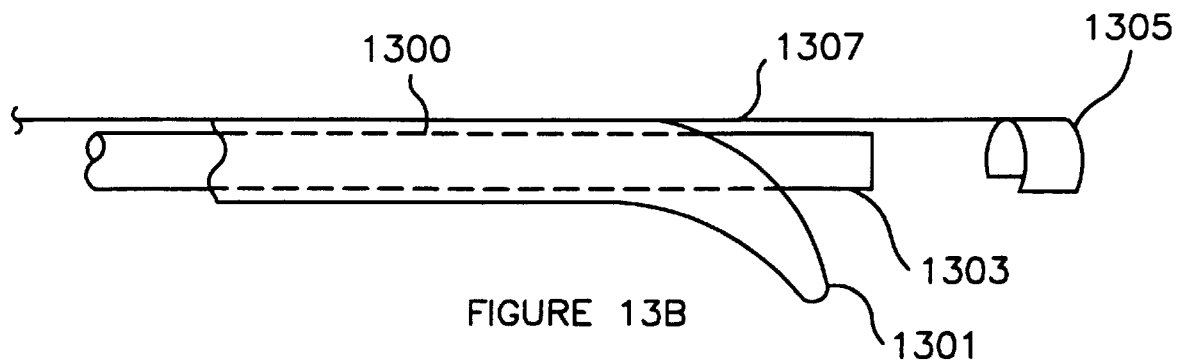

Referring now to FIGS. 13A and 13B, there are shown side views of retracted and extended configurations of another embodiment of the dissection cannula according to the present invention. This embodiment includes a blunt, tapered tip 1301 which deflects to one side of the endoscope 1303 to allow visualization outside of the cannula 1300 during vessel dissection and isolation. The dissection probe 1305 may reside adjacent to the cannula body 1300, proximal to the tapered tip 1301, and extend forward to dissect around the vessel being harvested and its side branches. The dissection probe shaft 1307 may run through a separate lumen in the cannula body 1300. The cannula body 1300 may contain an intrinsic curvature, and contain a port 1309 on the side of the cannula body near the tip, for exit of the endoscope 1303. The cannula body which has a normally curved configuration, straightens out upon introduction of a rigid, straight endoscope 1303. Partial retraction of the endoscope 1303 allows the cannula to curve, and the endoscope is advanced through the side port 1309 in the cannula body 1300 to view outside of the deflected cannula tip 1301.

Figure 17:
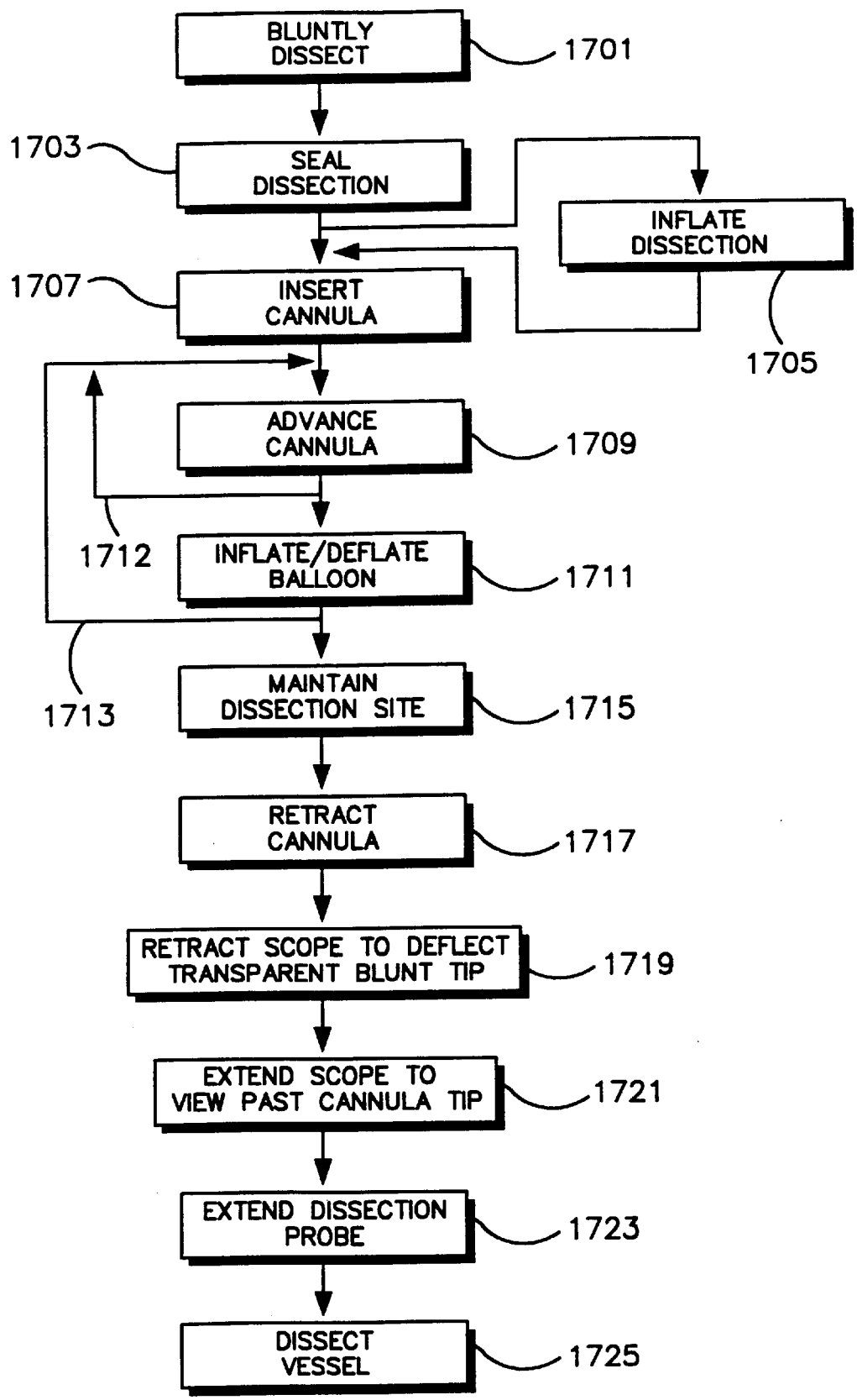
FIG. 17 is a flow chart illustrating the procedures involved with the cannula of FIGS. 13A and 13B.

A surgical procedure involving the cannula 1300 shown in FIG. 13 is illustrated in the flow chart of FIG. 17. Specifically, an initial incision and blunt dissection is performed 1701 to prepare an initial dissected cavity. The cavity may then be sealed 1703 in conventional manner and inflated 1705 to facilitate insertion of the cannula 1300 that is inserted into the cavity 1707 through a conventional gas-tight seal. The cannula is advanced 1709 and a perimeter balloon 128 on the cannula is inflated 1711 to expand the dissected cavity, and is then deflated to facilitate further advancement of the cannula and reinflation of the balloon. This sequence is repeated 1712, 1713 until the dissected cavity of sufficient size or length is formed along the vessel of interest. The dissected cavity is maintained 1715 by insufflation or mechanical traction or otherwise, as previously described, and the cannula may be retracted 1717 to a selected location in the cavity at which the endoscope 1303 may be retracted 1719 relative to the body of the cannula 1300 in order to permit deflection of the blunt tip 1301 away from the tip of the endoscope, as shown in FIG. 13B. Thereafter, the endoscope 1303 may be extended 1721 to view past the blunt tip 1301, and the dissection probe 1305 may also be extended 1723 and manipulated within the dissected cavity to dissect the vessel of interest 1725 from remaining connective tissue.

Figure 16:
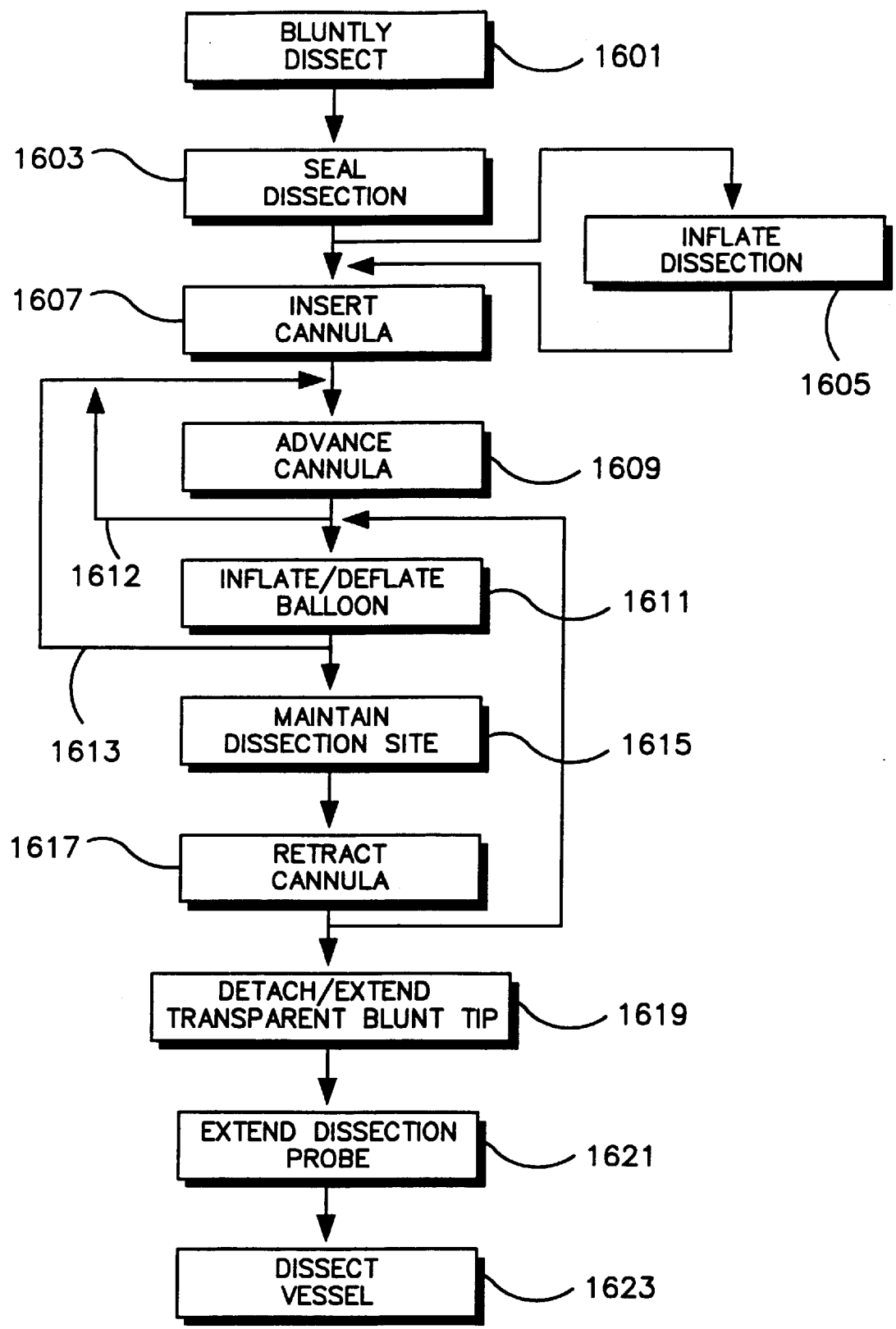
FIG. 16 is a flow chart illustrating the procedures involved with the cannula of FIGS. 9A and 9B.

Referring now to the flow chart of FIG. 16, a surgical procedure involving the cannula 900 shown in FIG. 9A includes making an initial incision and blunt dissection 1601 to form an initial dissected cavity. The cavity may then be sealed 1603 in conventional manner and inflated 1605 to facilitate insertion 1607 of the cannula 900 into the cavity through a conventional gas-tight seal. The cannula 900 is advanced 1609 and a perimeter balloon 901 on the cannula is inflated 1611 to expand the dissected cavity, and is deflated to facilitate further advancement of the cannula, and reinflation of the balloon. This sequence is repeated 1612, 1613 until the dissected cavity of sufficient size or length is formed along the vessel of interest. The dissected cavity is maintained 1615 in a manner as previously described, and the cannula 900 may be retracted 1617 sufficiently within the dissected cavity to facilitate detaching and/or extending 1619 the blunt tip 903 and facilitating extension 1621 of the dissection probe 907. One or more of the steps 1617, 1619, and 1621 may be repeated while dissecting connecting tissue 1623 to harvest the vessel of interest.

Therefore, the cannulas and dissection probes and associated surgical procedures facilitate blunt dissection of a working cavity along a vessel of interest, with visualization of the tissue being dissected through a blunt tip of transparent material and selected optical configuration positioned on the forward end of the cannula. Selective remote deployment and remote manipulation of a dissection probe carried on the cannula facilitates dissection of tissue around the vessel of interest and around side branch vessels along the vessel of interest being harvested from within and along the working cavity of dissected tissue.

I claim:

1. A cannula for dissecting an elongated cavity in tissue particularly along a course of a vessel, the cannula comprising:

a tubular body having animal end and a distal end;

at least one lumen extending within the length of the body between the proximal and distal ends thereof for receiving therein an endoscope, with viewing end disposed within the lumen near the distal end of the body;

a transparent tissue separating member substantially covering the distal end of the body and having a conically tapered outer surface converging toward a blunt tip disposed forward of the distal end of the body for directly contacting tissue, the member having substantially rigid and non-collapsible walls and having an internal surface that converges to a sharp point at a location substantially aligned with the viewing end of the endoscope for visualization thereby with reduced distortion through the walls of the member; and a tissue dilating element disposed on an exterior wall of the tubular body of the cannula near the distal end of the tubular body at a location thereon that is proximally spaced from the outer surface of the member for displacing tissue in contact therewith to a dimension greater than an outer dimension of the tubular body near the distal end thereof.

2. A cannula according to claim 1 in which the outer surface of the tissue separating member forms a -tapered outer surface converging toward a blunt tip having a radius of curvature substantially in the range of from approximately 0.030 inches to approximately 0.100 inches.

3. A cannula according to claim 2 in which the outer surface of the tissue separating member forms a blunt tip having a radius of curvature of approximately 0.045 inches.

4. A cannula for dissecting an elongated cavity in tissue particularly along a course of a vessel, the cannula comprising:

a tubular body having a proximal end and a distal end;

at least one lumen extending within the length of the body between the proximal and distal ends thereof;

a transparent tissue separating member substantially covering the distal end of the body and having a conically tapered outer surface converging toward a blunt tip disposed forward of the distal end of the body for directly contacting tissue, the member having substantially rigid and non-collapsible walls and having an internal surface that converges to a sharp point at a location substantially aligned with one lumen to facilitate visualization of tissue in contact with the walls of the member via an endoscope disposed with the one lumen, the member being selectively displaceable from the distal end of the body to expose the one lumen near the distal end of the body.

5. A cannula according to claim 4 comprising:

a tissue-dilating element attached to an exterior wall of the tubular body of the cannula near the distal end of the tubular body at a location thereon that is proximally spaced from the outer surface of the member for displacing tissue in contact therewith to a dimension greater than an outer dimension of the tubular body near the distal end thereof.

6. A cannula according to claim 1 or 4 in which the conically tapered outer surface to the blunt tip is about 0.5 inches in length.

7. A cannula according to claim 1 in which the dimension of the member at the distal end of the tubular body is about 8 millimeters.

8. A cannula according to claim 4 including a balloon disposed on an exterior wall of the tubular body near the distal end thereof at a location thereon that is proximally spaced from the outer surface of the member for selectively displacing tissue in contact therewith in response to fluid pressurization and expansion thereof to a dimension greater than an outer dimension of the tubular body near the distal thereof.

9. A cannular according to claim 1 in which the tissue dilating member includes a balloon for selectively displacing tissue in contact therewith in response to fluid pressurization and expansion thereof to a dimension greater than an outer dimension of the tubular body near the distal end thereof.

10. A cannula for dissecting an elongated cavity in tissue particularly along a course of a vessel, the cannula comprising:

a tubular body having a proximal end and a distal end;

at least one lumen extending within the length of the body between the proximal and distal ends thereof;

an edoscope having a lighted, viewing end disposed within the lumen near the distal end of the body; and a transparent tissue separating member substantially covering the distal end of the body and having a conically tapered outer surface converging toward a blunt tip disposed forward of the distal end of the body for directly contacting tissue, the member having an internal surface that converges to a cusp at a location substantially aligned with the viewing end of an endoscope to reduce distortion of visualization through the member, the member being selectively displaceable from the distal end of the body to expose the one lumen near the distal end of the body.

11. A cannula according to claim 10 in which the tissue separating member rotatably attaches to the distal end of the body for selective rotational detachment of the member from the body.

12. A method for dissecting an elongated cavity in tissue along a selected course in the body of a patient using a cannula having a transparent tissue-dissecting tip and a tissue dilating element disposed on an exterior wall of the cannula near a distal end thereof and including an endoscope disposed within the body for visualization through the tip, the method comprising:

forming an initial incision and bluntly dissecting an initial cavity at a location in the body of the patient;

inserting and advancing the cannula for separating tissue about the tip as visualization through the endoscope and tip;

selectively advancing the tissue dilating element and displacing tissue therewith to enlarge the cavity in separated tissue; and selectively displacing the tip relative to the body of the cannula to expose the distal end thereof.

13. The method according to claim 12 including:

forming a counterincision at a selected location along the cavity;

positioning the tip and selected portion of the cannula through the counterincision; and removing the tip exposed through the counterincision from the body of the cannula.

14. A cannula for dissecting an elongated cavity in tissue particularly along a course of a vessel, the cannula comprising:

a rigid tubular body having a proximal end and a distal end of selected sectional dimension;

at least one lumen extending within the length of the body between the proximal and distal ends thereof for receiving therein an endoscope with a viewing end disposed within the lumen near the distal end of the body;

a tissue separating member substantially covering the distal end of the body and having an outer surface that converges toward a blunt tip disposed forward of the distal end of the body for directly contacting tissue to be directed, the member having substantially rigid walls with a portion thereof that is transparent aligned with a viewing end of an endoscope within the one lumen for visualization thereby of tissue directly contacting the transparent portion of the outer surface; and a tissue dissecting element disposed on an exterior wall of the tubular body of the cannula near the distal end of the tubular body at a location thereon that is proximally spaced from the blunt tip of the member and having an outer dimension greater than the selected sectional dimension of the distal end for displacing tissue in contact therewith to a dimension greater than the selected sectional dimension of the tubular body near the distal end thereof.

15. A cannula according to claim 14 in which the member and element disposed near the distal end of the tubular body form a tissue dissecting structure for displacing tissue to a greater dimension than said selected sectional dimension.

16. A cannula according to claim 14 in which the outer surface to the blunt tip tapers over a length of about 0.5 inches.

17. A cannula according to claim 14 in which the outer dimension of the member at the distal end of the tubular body is about 8 millimeters.

18. A cannula according to claim 17 in which the outer dimension of at least the element is greater than the selected sectional dimension of the distal end of the tubular body.

19. A method for dissecting an elongated cavity in tissue along a selected course in the body of a patient using a cannula having a transparent tissue-dissecting tip forming a tissue dissecting element disposed near a distal end of the cannula of selected sectional dimension and including an endoscope disposed within the body for visualization through the tip, the method comprising:

forming an initial incision and bluntly dissecting an initial cavity at a location in the body of the patient;

inserting and advancing the cannula for separating tissue about the tip as visualized through the endoscope and tip; and selectively advancing the tissue-dissecting tip and displacing tissue therewith to enlarge the cavity in separated tissue to greater sectional dimension than the selected sectional dimension of the cannula near the distal end thereof.

* * * * *

UNITED STATES PATENT AND TRADEMARK OFFICE
CERTIFICATE OF CORRECTION

PATENT NO. : 6,277,137 B1
DATED : August 21, 2001
INVENTOR(S) : Albert K. Chin

It is certified that error appears in the above-identified patent and that said Letters Patent is hereby corrected as shown below:

Column 14,
Line 26, delete "animal" and insert -- proximal --;

Column 15,
Line 26, delete "cannular" and insert -- cannula --;
Line 38, delete "edoscope" and insert -- endoscope --.

Signed and Sealed this

Third Day of December, 2002

JAMES E. ROGAN
*Director of the United States Patent and Trademark Office*